United States Patent
Fu et al.

(10) Patent No.: US 12,285,314 B2
(45) Date of Patent: Apr. 29, 2025

(54) METHODS OF DEPOSITING SILVER NANOSTRUCTURES ON TO IMPLANT SURFACES

(71) Applicant: Biomet 3i, LLC, Palm Beach Gardens, FL (US)

(72) Inventors: Cong Fu, Palm Beach Gardens, FL (US); Elnaz Ajami, Palm Beach Gardens, FL (US); Hai Bo Wen, Lake Worth, FL (US); Olga S. Sanchez, Wellington, FL (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/338,002

(22) Filed: Jun. 20, 2023

(65) Prior Publication Data

US 2023/0346521 A1    Nov. 2, 2023

Related U.S. Application Data

(62) Division of application No. 16/502,781, filed on Jul. 3, 2019, now abandoned.

(60) Provisional application No. 62/694,600, filed on Jul. 6, 2018.

(51) Int. Cl.
| | | |
|---|---|---|
| *A61C 8/00* | (2006.01) | |
| *A61K 9/00* | (2006.01) | |
| *A61K 33/00* | (2006.01) | |
| *A61K 33/38* | (2006.01) | |
| *B82Y 30/00* | (2011.01) | |
| *B82Y 5/00* | (2011.01) | |

(52) U.S. Cl.
CPC .......... *A61C 8/0013* (2013.01); *A61K 9/0063* (2013.01); *A61K 33/00* (2013.01); *A61K 33/38* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | |
|---|---|---|
| 2014/0272791 A1 | 9/2014 | Sanchez et al. |
| 2016/0000533 A1 | 1/2016 | Rodriguez et al. |
| 2017/0014210 A1 | 1/2017 | Rogers et al. |
| 2017/0042682 A1 | 2/2017 | Mandanici et al. |
| 2017/0173213 A1* | 6/2017 | Yates ............ C25D 9/04 |
| 2020/0008909 A1 | 1/2020 | Fu et al. |

FOREIGN PATENT DOCUMENTS

| | | |
|---|---|---|
| CN | 108181363 | 6/2018 |
| CN | 108181363 A * | 6/2018 |
| EP | 2962657 | 1/2016 |
| KR | 101458018 | 11/2014 |
| WO | WO 2007/149386 | 12/2007 |
| WO | WO 2015/138387 | 9/2015 |

OTHER PUBLICATIONS

Machine translation of CN108181363A (Year: 2024).*
"Database WPI Week 201476 Thomson Scientific, London, GB", (Nov. 4, 2014), 2 pages.
"Database WPI Week 201848 Thomson Scientific, London, GB; AN 2018-50296U", (Jun. 21, 2013), 2 pages.
"Dental Implant and Osseointegration Success Tips," Harmony Dental Care, available at https://www.harmonydentalcare.com/dental-implants/dental-implant-and-osseointegration-success-tips/, accessed Jun. 4, 2022), 44S-51S.
"Threshold," Cambridge Dictionary, https://dictionary.cambride.org/us/dictionary/english/threshold, accessed Nov. 29, 2022.
Derks et al., "Effectiveness of Implant Therapy Analyzed in a Swedish Population: Early and Late Implant Loss," JDR Clinical Research Supplement, Mar. 2015, vol. 94(3)(Supp 1), 8 pages.
Noronha et al., "Silver nanoparticles in dentistry," Dental Materials, Oct. 2017, vol. 33(10), pp. 1110-1126.
Official Action for Canadian Patent Application No. 3,048,565, dated Jul. 6, 2020 4 pages.
"European Application Serial No. 19184383.8, Extended European Search Report mailed Nov. 29, 2019", 7 pages.
Official Action for European Patent Application No. 19184383.8, dated Feb. 16, 2021 7 pages.
Official Action for European Patent Application No. 19184383.8, dated Dec. 6, 2022 7 pages.
Official Action for U.S. Appl. No. 16/502,781, dated Mar. 29, 2022 8 pages, Restriction Requirement.
Official Action for U.S. Appl. No. 16/502,781, dated Jun. 9, 2022 9 pages.
Final Action for U.S. Appl. No. 16/502,781, dated Dec. 5, 2022 13 pages.
Official Action for U.S. Appl. No. 16/502,781, dated Mar. 20, 2023 11 pages.

* cited by examiner

*Primary Examiner* — H. Sarah Park
(74) *Attorney, Agent, or Firm* — Sheridan Ross P.C.

(57) ABSTRACT

Methods of depositing nanoparticles onto a substrate (e.g., an implant) are provided, as are the resulting substrates (e.g., implants) formed by such deposition methods. The nanoparticles can be silver nanoparticles that provide antimicrobial or antibacterial properties to the substrate.

17 Claims, 7 Drawing Sheets

METHODS OF DEPOSITING SILVER NANOSTRUCTURES ON TO IMPLANT SURFACES

CLAIM OF PRIORITY

This application is a divisional of U.S. patent application Ser. No. 16/502,781, filed Jul. 3, 2019; which claims the benefit of U.S. Provisional Patent Application No. 62/694,600, filed on Jul. 6, 2018; the benefit of priority of which is claimed hereby, and which is incorporated by reference herein in its entirety.

FIELD OF THE DISCLOSURE

The present disclosure relates to methods of depositing nanostructures onto implant surfaces, and the implants produced by such methods.

BACKGROUND

Implant associated infections can present a significant burden to both the patient and the economy. In oral implantology, inflammation and infection of the peri-implant tissue is a major concern, as it can lead to progressive bone loss around the implant and subsequent implant failure. In a study which evaluated rates of dental implant loss and peri-implantitis, it was found 14.5% of patients exhibited moderate/severe peri-implantitis at the 9-year examination. (See e.g., Derks, J. (2015). Effectiveness of implant therapy in Sweden, University of Gothenburg, Gothenburg, Sweden).

Bacterial infections are the result of bacterial adhesion and proliferation on the implant surface. The competition between osseointegration with healthy tissue and colonization of bacteria onto the implant surface is critical to the long-term success of the implant. For a successful implantation, bacterial colonization must be prevented before tissue integration.

To prevent bacterial colonization, both "passive" and "active" methods can be considered. For example, the physiochemical properties of surfaces can be modified to form unfavorable environment for bacterial adhesion. However, the effectiveness of such "passive" methods strongly depend on bacteria species, and therefore may not be applicable to all bacteria types.

Clinically, to reduce the incidence of bacterial film formation on implant surfaces, local delivery of antibiotics can be desirable. Compared with systemic treatments, local delivery can have numerous advantages in terms of therapeutic efficiency and tolerance. Local release can result in a high and sustained concentration of antibiotics to prevent the risk of recurrence. Furthermore, in local delivery, the high doses administered can be better tolerated by the patient. However, one of the major concerns with the use of antibiotics is the relatively rapid rate that bacteria can become resistant to treatment. There is evidence that local delivery of antibiotics significantly increases the likelihood of infection with antibiotic resistant bacteria following implant revision surgery. Moreover, many antibiotics operate specifically and show limited efficacy against certain bacterial strains. Thus, other antibacterial agents that act more broadly against a wide range of bacteria have been pursued as an alternative strategy.

The present disclosure provides improved deposition structures and methods to prevent bacterial colonization, while allowing osseointegration at the appropriate time.

SUMMARY

Various deposition methods are disclosed. According to one example an electrochemical deposition process is disclosed, which reduces silver ions in the electrolyte solution to metallic silver particles. Simultaneously with this reduction of silver ions, the silver particles can be deposited onto an underlying substrate. According to another example, an electroless deposition process is disclosed, which can generate a silver coated surface by immersing the substrate into silver-rich environment. This process can include an ion exchange that happens between silver ions in the solution and elements on a surface of the substrate. According to yet another example, silver compounds can be incorporated into drug carriers, such as a pH sensitive polymer. Then the release of the compounds can be triggered by the conditions of the surrounding environment and can be controlled by the degradation of the carriers.

To better illustrate the apparatuses, methods and systems disclosed herein, a non-limiting list of examples is provided here:

In Example 1, a dental implant optionally can comprise: a body including an external surface positioned to contact a jawbone of a patient when the dental implant is implanted, a majority of the external surface can be coated with silver nanoparticles, wherein the silver nanoparticles can be configured to provide antimicrobial properties to the dental implant.

In Example 2, the dental implant of Example 1, wherein the nanoparticles can be between 0.1 nm and 100 nm in at least one dimension, inclusive.

In Example 3, the dental implant of Example 1, wherein substantially all of the external surface can be coated with the silver nanoparticles.

In Example 4, the dental implant of Example 3, wherein substantially all exposed surfaces of the dental implant can be coated with the silver nanoparticles.

In Example 5, the dental implant of Example 1, wherein an amount by weight percentage of the silver nanoparticles can be between 0.1 % and 25.0 %, inclusive.

In Example 6, the dental implant of Example 1, wherein the silver nanoparticles can have broad spectrum antimicrobial properties against Gram-negative and Gram-positive bacteria, and a low microorganism resistance probability.

In Example 7, a method of depositing nanoparticles on a dental implant that can optionally comprise: preparing an electrolyte solution comprising an aqueous solution having silver nitrate ($AgNO_3$); positioning the dental implant within the electrolyte solution; and applying an electric current to the electrolyte solution for a duration of time, thereby causing deposition of silver nanoparticles on a surface of the dental implant, the silver nanoparticles providing antimicrobial properties to the dental implant.

In Example 8, the method of Example 7, wherein the aqueous solution can have a concentration of between about 0.01 mM to about 50 mM, inclusive, $AgNO_3$.

In Example 9, the method of any one or any combination of Examples 7-8, can further comprise preparing the electrolyte solution so that the aqueous solution additionally has $NaNO_3$.

In Example 10, the method of Example 9, wherein the aqueous solution can have a concentration of between about 0.1 mM to about 1000 mM, inclusive, $NaNO_3$.

In Example 11, the method of any one or any combination of Examples 7-10, can further comprise maintaining a temperature of the electrolyte solution at anywhere between about 18-30° C. during the deposition step.

In Example 12, the method of Example 9, can further comprise stifling the aqueous solution at a rate of anywhere between about 100-1000 RPM prior to the deposition step.

In Example 13, the method of any one or any combination of Examples 7-12, can further comprise placing the dental implant through an ultrasonication process to remove nanoparticles over a certain size threshold from the surface of the dental implant.

In Example 14, the method of Example 9, can further comprise controlling one or more of the following deposition parameters to control the size, quantity, and/or deposition location of silver nanoparticles on the surface of the dental implant: (i) deposition time, (ii) electrolyte solution temperature, (iii) the amount of electric current applied to the electrolyte solution, (iv) $AgNO_3$ concentration, and (v) $NaNO_3$ concentration.

In Example 15, a method implanting a dental implant can optionally comprise: forming a bore in a jaw of a patient; and implanting the dental implant into the bore at an implantation location, the dental implant including a coating of silver nanoparticles on a surface of the dental implant, the silver nanoparticles being configured to dissolve over time and provide an antimicrobial effect within the patient at the implantation location.

In Example 16, the method of Example 15, wherein the silver nanoparticles can have broad spectrum antimicrobial properties against Gram-negative and Gram-positive bacteria, and a low microorganism resistance probability.

In Example 17, the method of any one or any combination of Examples 15-16, wherein a majority of the dental implant can be coated with the silver nanoparticles.

In Example 18, the method of any one or any combination of Examples 15-17, wherein an amount by weight percentage of the silver nanoparticles can be between 0.1 % and 25.0 %, inclusive.

In Example 19, the method of any one or any combination of Examples 15-18, wherein the nanoparticles can be between 0.1 nm and 100 nm in at least one dimension, inclusive.

In Example 20, the method of any one or any combination of Examples 15-19, wherein coating of silver nanoparticles on the surface of the dental implant can include coating substantially all of the external surface with the silver nanoparticles.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the examples are not intended to be limited to any specific terms used herein, and it is to be understood that each specific term includes all technical equivalents.

The present disclosure is directed to methods for depositing nanostructures onto implant surfaces, and the implants resulting from such methods. The methods can involve depositing silver or silver compound nanostructures on implant surfaces to, for example, improve the antimicrobial characteristics thereof, while keeping any osseointegration characteristics intact. The silver or silver compound nanostructures can alleviate a number of downsides to current antimicrobial techniques, as detailed more fully below.

Figure 1:
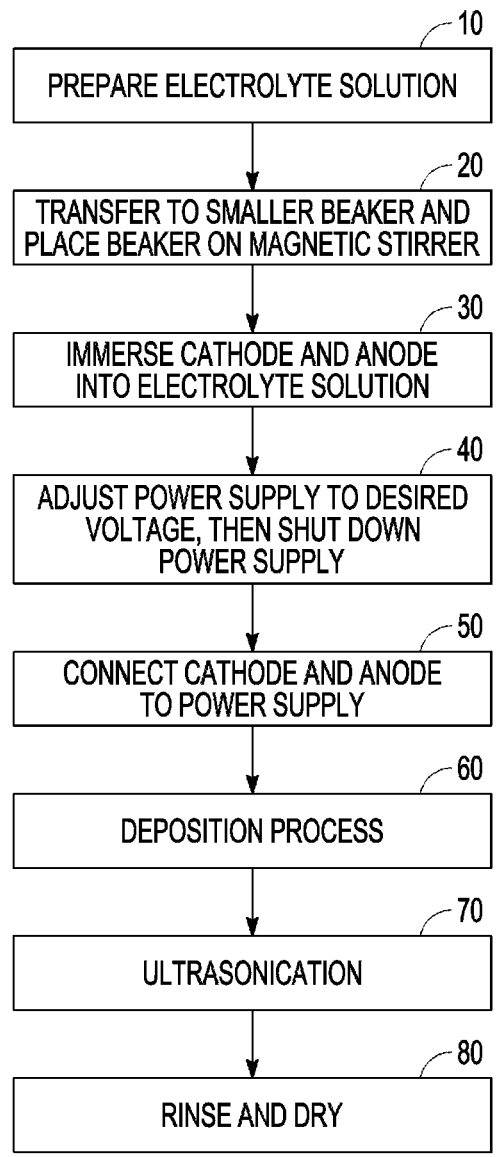
FIG. 1 depicts a flow chart illustrating a method of depositing nanostructures on an implant surface.
Figure 2A:
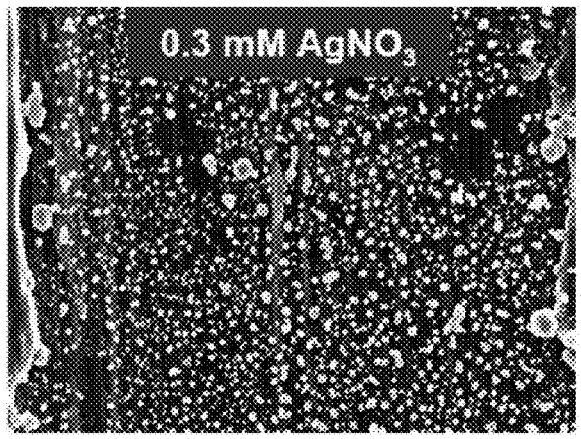
FIGS. 2A-E illustrate a first example of the deposition method of FIG. 1, where the concentration of silver nitrate ($AgNO_3$) is varied.
Figure 2B:
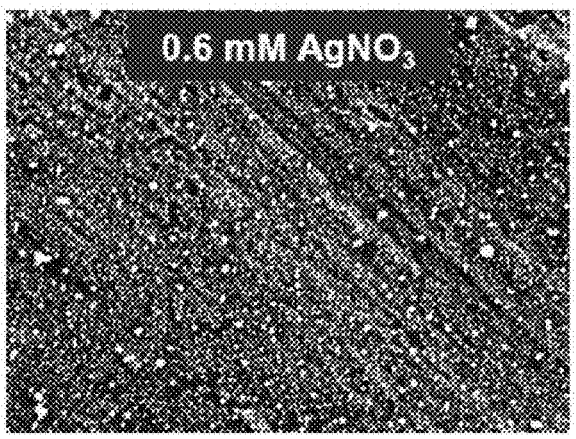
Figure 2C:
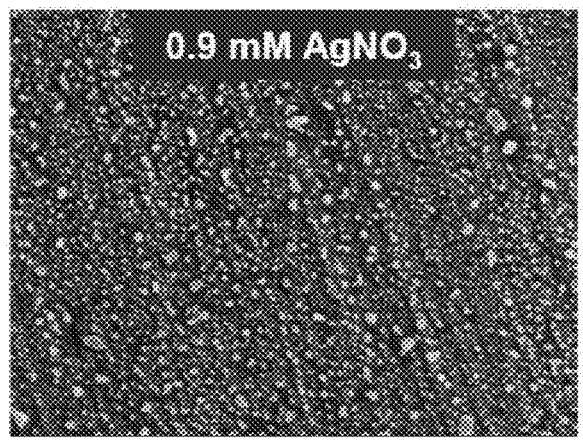
Figure 2D:
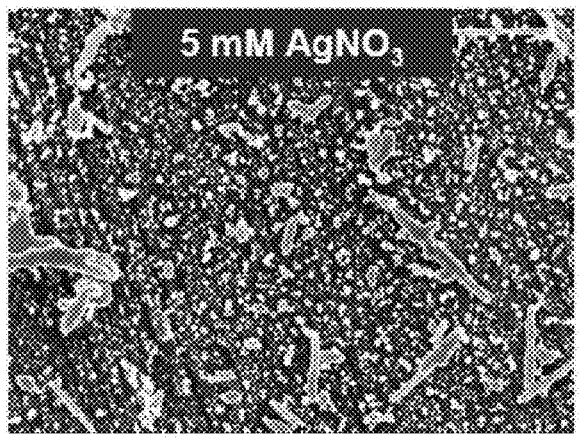
Figure 2E:
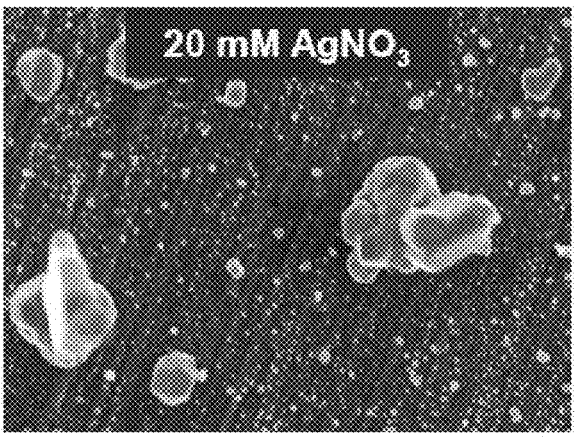

FIG. 1 illustrates a flow chart depicting a method for depositing nanostructures onto an implant surface. In a merely exemplary embodiment, first an electrolytic solution 10 can be prepared. The electrolyte solution can comprise an aqueous solution having about 0.01 mM to about 50 mM silver nitrate ($AgNO_3$). In an example, about 0 mM $NaNO_3$ to about 1000 mM $NaNO_3$ can also be added to the solution to, for instance, increase the conductivity of the electrolyte solution. $NaNO_3$ is not needed in all cases, and thus, can be 0 nM in some cases. According to one example, 138 mM $NaNO_3$ can be utilized. The solution can be kept at or near room temperature (anywhere between about 18-30° C.), although it is to be appreciated that other temperatures can be employed, as described below. In some examples, the electrolyte solution might only comprise silver nitrate ($AgNO_3$) and not $NaNO_3$.

As illustrated at step 20, the electrolyte solution can then be transferred to a beaker or other container. The beaker or container can, in an example, be placed on a magnetic stirrer or another agitation device can be used. At step 30 an anode (e.g., Pt) and a cathode (e.g., Ti (i.e. commercially pure Ti, Ti alloy, TiAl alloy (e.g., $Ti_6Al_4V$)), stainless steel, tantalum, etc.) can be placed onto a fixture (e.g., Teflon). In an example, the anode and cathode can be separated by some predetermined distance (e.g., anywhere between about 0.25-3 cm) by the fixture.

At step 30, the anode and cathode can be immersed into the electrolyte solution, and the stirrer or agitation device can be activated to stir or mix the solution at a rate of anywhere between about 100-1000 RPM, in a particular embodiment anywhere between about 300-500 RPM. At step 40, a power supply connected to the anode and cathode can be adjusted to a desired voltage. In an example, the power supply can be set to anywhere between about 2-25V with a 2+/−0.2 AMP maximum output. In addition, the power supply can be shut down at step 40 so that, at step 50, the anode and cathode can be connected to the power supply (e.g., with silver and platinum wires, respectively).

Step 60 can commence the electrochemical deposition process. First, a substrate can be placed in the electrolyte solution. The substrate can include a surface that can be machined, acid etched, grit blasted and acid etched, and/or with nano-complexity such as nanotubes or Discrete Crystalline Deposition (DCD®), as provided by the Applicant. Certain exemplary substrates are described in more detail below.

In an example, the deposition process can next involve setting the temperature of the electrolyte solution to anywhere between about 0-100° C., turning the power supply on, and applying an electric current to the system (e.g., anode and cathode, immersed in the electrolyte solution). The electric current can be applied for anywhere between about 30 seconds to 1 hour, in an example. Other time durations are possible. Application of an electric current within the ranges mentioned above can be applied to the electrolyte solution for the aforementioned time, causing deposition of silver nanoparticles onto the substrate immersed in the electrolytic solution.

In an example, the substrate can be an implant. In a further example, the substrate can be a dental implant designed to be implanted into a patient's jawbone. For instance, the dental implant can include any of the features or characteristics of U.S. Patent Pub. No. 2014/0272791, filed by Zimmer Dental, Inc., the disclosure of which is hereby incorporated by reference herein in its entirety. Of course, the substrate can be a dental implant that has different features than the dental implant of the '791 Publication.

The deposition of silver nanoparticles can occur on an external surface of the implant that is arranged to contact the patient's jawbone (e.g., outer surface of implant body 17 of the '791 Publication). Alternatively, or in addition, the silver nanoparticles can be deposited on a majority of the aforementioned external surface of implant body 17, or a portion of the external surface that is less than a majority. In a further alternative, the silver nanoparticles can be deposited on substantially all of the surfaces of implant body 17 that are exposed within the electrolyte solution. In an example, this can mean that substantially all of the outer surfaces of implant body 17 can include deposited silver nanoparticles, according to the above process. It is to be appreciated that the application of an electric current in the electrolytic solution detailed above can reduce silver ions to nanostructures and deposit the silver nanostructures onto surfaces of the substrate (e.g., dental implant). In yet further examples, the silver nanoparticles can be deposited on various other components and/or other surfaces such as an implant/abutment junction, a provisional abutment external surface, a definitive abutment external surface, internal surfaces that can be accessed, etc.).

By "nanostructures" or "nanoparticles", it is meant that such particles have either one, two or all three dimensions in the nanoscale range of 0.1 nm to 100 nm, inclusive. The nanostructures or nanoparticles can either be in a single particulate or agglomerate to form a cluster.

At step 70, an ultrasonication process can take place. In an example, step 70 can be omitted. The ultrasonication process can optimize the size distribution of silver nanostructures by removing some large particles from the surface of the substrate. In other words, using an ultrasonication process, particles over a certain size threshold (e.g., 50 nm to 500 nm, inclusive) can be removed from the substrate by applying ultrasonic energy to the substrate. This can have the effect of ensuring an optimal size distribution of silver nanostructures on the substrate.

In step 80, the substrate can be rinsed in a reverse osmosis/deionized water (RO/DI water). The substrate can then be dried (e.g., in an oven) at a temperature of about 100+/−5° C. for about 30+/−10 minutes.

Deposition of silver nanoparticles onto the surface of a substrate (e.g., dental implant) can have a number of benefits. Silver ions, compounds, and particles have antibacterial properties that can be used as an alternative to antibiotic therapy. Bacteria can be killed upon surface contact with metallic silver nanoparticles, and through the extended release of low concentrations of silver ions through oxidative dissolution of the nanoparticles. The advantages of using silver as an antimicrobial agent can include: (1) it has broad spectrum antimicrobial activities against Gram-negative and Gram-positive bacteria, (2) it has high efficiency and low toxicity for long-term use, and (3) as an alternative to traditional antibiotic molecules, silver has a low probability of a microorganism developing resistance. The foregoing is a non-exhaustive list of the benefits of using silver nanoparticles in the context of the present invention.

In addition to the aforementioned benefits, an additional positive to the deposition method of the present disclosure is that the antimicrobial agent (silver nanostructures) can be coated onto the substrate (e.g., dental implant) without requiring any specific pre-treatment of the target surface of the substrate. Further, the silver nanostructures are in nanoscale. Due to the high specific surface area of nanostructures, bacteria can be killed more effectively. Furthermore, since the coating can be deposited by an electrochemical procedure, as described above, a uniform distribution of silver nanostructures can be created while the size and quantity of the nanostructures can be well controlled. Therefore, the amount of silver can be maintained between minimum effective level and maximum safety level. As disclosed herein, the minimum effective level for silver ion concentration can be as low as 1.43 ppm (ppm and ug/ml are equivalent). This minimum effective level is sufficient to kill or inhibit a wide range of microorganisms. As disclosed herein, the maximum safety level can be as high as 112.03 ug/ml.

Applicant sets forth several particular examples of the deposition process detailed above using different substrates and different deposition parameters. Such examples are illustrated in FIGS. 2A-7B, and disclosed in more detail below. It is to be understood that the examples are non-limiting, and are illustrative of how different parameters of the deposition process and/or the substrate can affect the ultimate result.

EXAMPLES 1A-E

FIGS. 2A-E illustrate Examples 1A-E of the present disclosure, respectively. The deposition parameters for Examples 1A-E are shown in Table 1.1 below.

TABLE 1.1

| Deposition Temp | $NaNO_3$ Concentration | Voltage | Deposition Time | Variable |
| --- | --- | --- | --- | --- |
| About Room Temp | 1.25 mM (low) | 5 V | 90 seconds | $AgNO_3$ Concentration |

As shown above, Examples 1A-E, illustrated in FIGS. 2A-E, respectively, demonstrate the effect of varying the $AgNO_3$ concentration of the electrolytic solution during the deposition process outlined above. It was observed that large crystals were formed when a high concentration of $AgNO_3$ was added into the electrolytic solution for deposition. This can be seen in FIGS. 2A-E, which have the $AgNO_3$ concentration listed with each figure. As such, Applicant can, in an example, vary the $AgNO_3$ concentration in the electrolytic solution to change the size and/or amount of silver crystals or particles deposited on the substrate (e.g., dental implant), using the deposition process detailed above. In Examples 1A-E, a machined surface was used as a deposition substrate to illustrate the effect of varying the $AgNO_3$ concentration of the electrolyte solution.

Further, the following weight percentages in Table 1.2 were measured by energy-dispersive x-ray spectroscopy (EDS) (n=5 per sample):

TABLE 1.2*

| Deposition Amount | .3 mM $AgNO_3$ | .6 mM $AgNO_3$ | .9 mM $AgNO_3$ |
|---|---|---|---|
| Weight Percentage of Silver | 0.12 +/− 0.24% | 1.00 +/− 1.84% | 0.93 +/− 0.10% |

*EDS was not conducted on 5 and 20 mM concentrations of $AgNO_3$.

The above Table 2.2 confirms that, with increased silver ion concentrations in the electrolyte solution, an increase in the amount of deposited silver nanoparticles can be expected on the substrate. Thus, to modify the above deposition process in terms of amount of deposited silver nanoparticles, it is possible to vary the concentration of $AgNO_3$ in the electrolyte solution.

EXAMPLES 2A-C

Figure 3A:
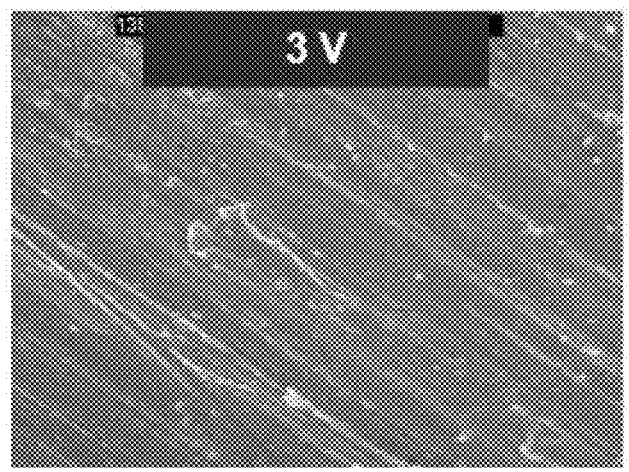
FIGS. 3A-C illustrate a substrate processed according to a second example of the deposition method of FIG. 1, where the voltage applied during the deposition process was varied.
Figure 3B:
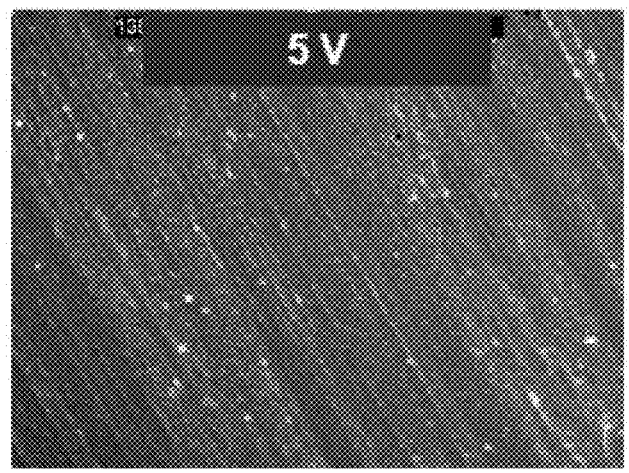
Figure 3C:
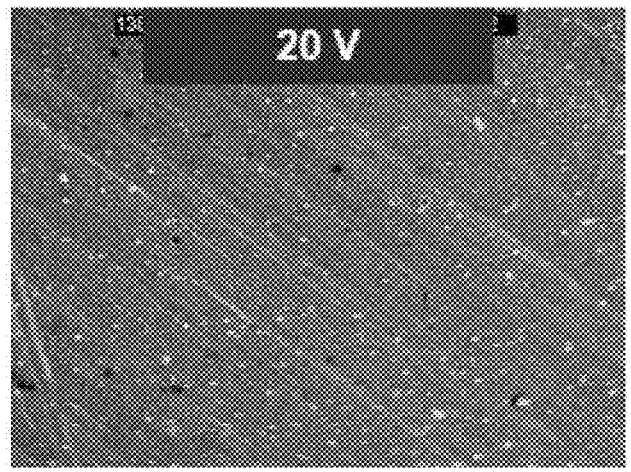

FIGS. 3A-C illustrate Examples 2A-C of the present disclosure, respectively. The deposition parameters for Examples 2A-C are shown in Table 2.1 below.

TABLE 2.1

| Deposition Temp | $AgNO_3$ Concentration | $NaNO_3$ Concentration | Deposition Time | Variable |
|---|---|---|---|---|
| About Room Temp | 0.9 mM | 138 mM | 90 seconds | Voltage (potentiostatic) |

As shown above, Examples 2A-C, illustrated in FIGS. 3A-C, respectively, demonstrate the effect of varying the voltage applied to the electrolytic solution during the deposition process outlined above. The voltage applied to the electrolytic solution is set forth above each respective figure. It was observed that an increase in deposition voltage under potentiostatic mode resulted in an increase in the quantity of silver nanoparticles based on visual inspection of Scanning Electron Microscopy (SEM) images. As such, it is possible to also vary the voltage applied to the electrolytic solution in the above deposition process to alter the quantity of silver nanoparticles deposited to the substrate (e.g., dental implant). In Examples 2A-C, a machined surface was used as a deposition substrate, similar to as in Examples 1A-E.

EXAMPLES 3A-C

Figure 4A:
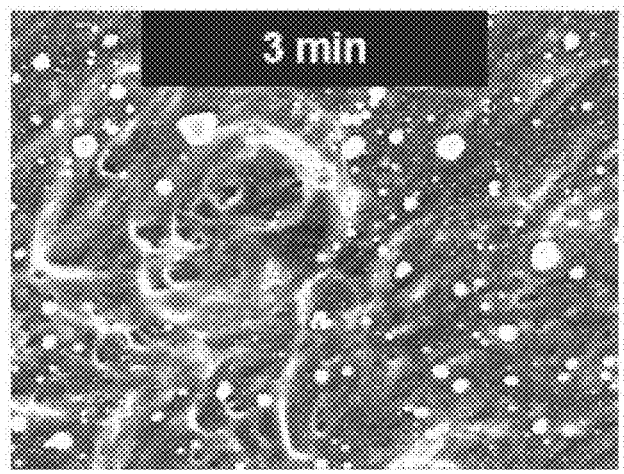
FIGS. 4A-C illustrate a substrate processed according to a third example of the deposition method of FIG. 1, where the deposition time was varied.
Figure 4B:
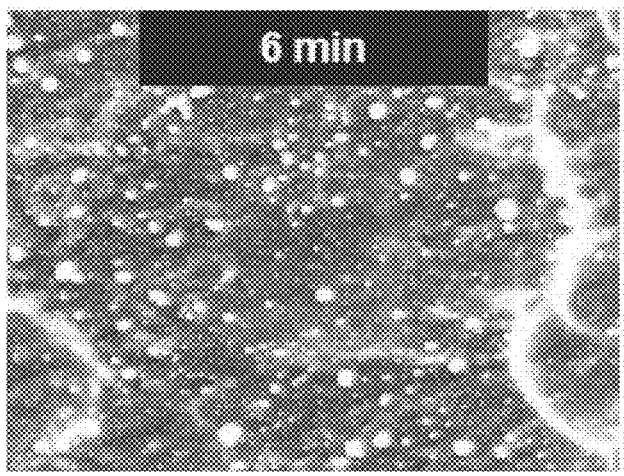
Figure 4C:
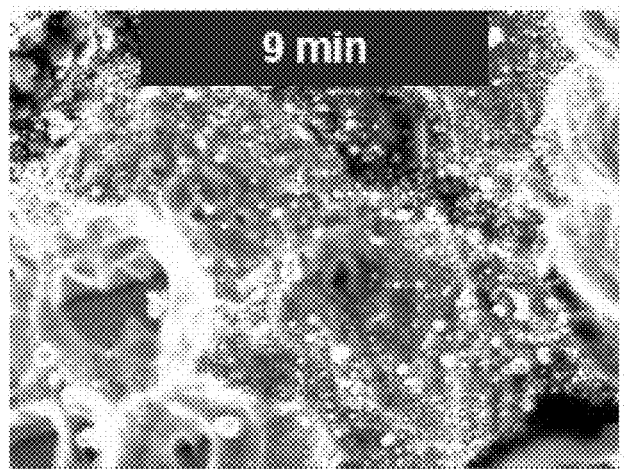

FIGS. 4A-C illustrate Examples 3A-C of the present disclosure, respectively. The deposition parameters for Examples 3A-C are shown in Table 3.1 below.

TABLE 3.1

| Deposition Temp | $AgNO_3$ Concentration | $NaNO_3$ Concentration | Voltage | Variable |
|---|---|---|---|---|
| About Room Temp | 0.9 mM | 138 mM | 5 V | deposition time |

As shown above, Examples 3A-C, illustrated in FIGS. 4A-C, respectively, demonstrate the effect of varying the deposition time during the deposition process outlined above. The deposition time is set forth above each respective figure. It was observed that a higher amount of silver nanoparticles was deposited on the substrate (e.g., dental implant) with increased deposition time. Indeed, EDS results demonstrated that the amount by weight percent of silver deposited on the substrate is as shown in the below Table 3.2. The deposition substrate used was an acid etched surface.

TABLE 3.2

| Deposition Amount | 3 Minute Deposition | 6 Minute Deposition | 9 Minute Deposition |
|---|---|---|---|
| Weight Percentage of Silver | 0.26 +/− 0.52% | 1.75 +/− 1.29% | 2.91 +/− 1.50% |

Thus, it is possible to vary the deposition time in the deposition process set forth above to increase or decrease the amount of silver nanoparticles deposited on the substrate (e.g., dental implant).

EXAMPLES 4A-D

Figure 5A:
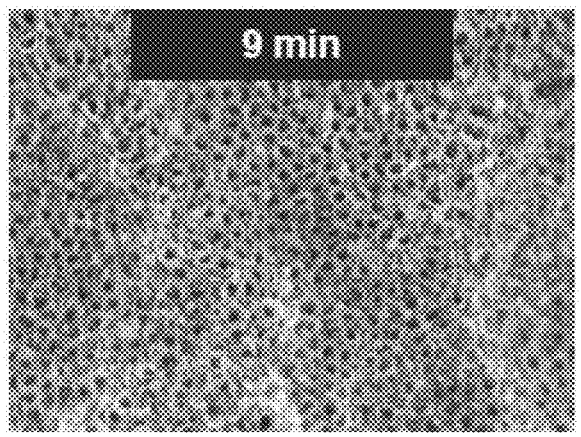
FIGS. 5A-D illustrate a substrate processed according to a fourth example of the deposition method of FIG. 1, where the deposition time was varied and the substrate includes a nanotube structure.
Figure 5B:
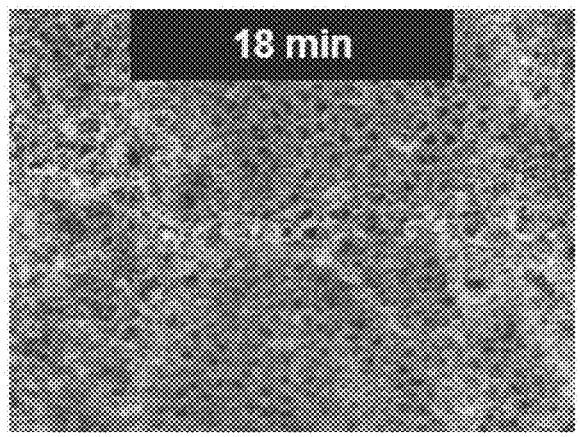
Figure 5C:
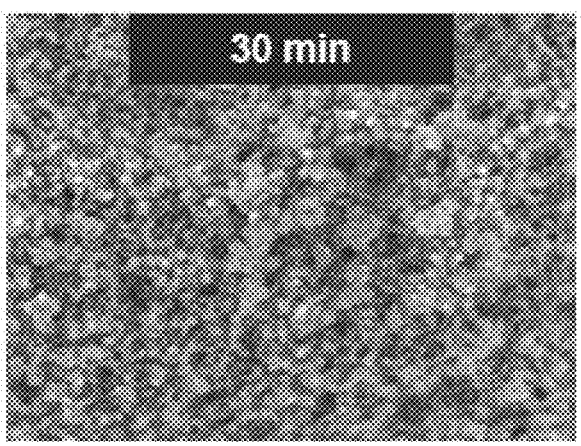
Figure 5D:
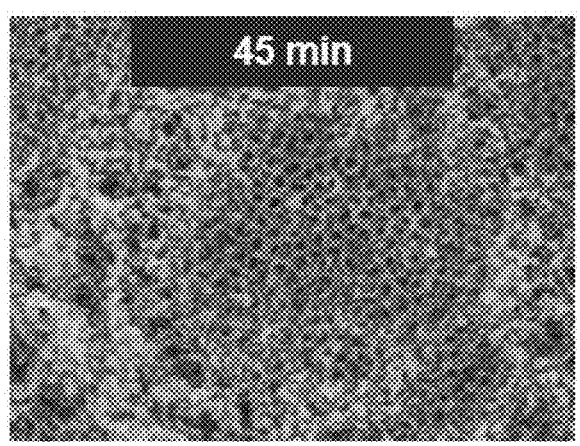

FIGS. 5A-C illustrate Examples 4A-D of the present disclosure, respectively. The deposition parameters for Examples 4A-D are shown in Table 4.1 below.

TABLE 4.1

| Deposition Temp | $AgNO_3$ Concentration | $NaNO_3$ Concentration | Voltage | Variable |
|---|---|---|---|---|
| About Room Temp | 0.9 mM | 138 mM | 5 V | deposition time |

As shown above, Examples 4A-D, illustrated in FIGS. 5A-C, respectively, demonstrate the effect of varying the deposition time during the deposition process outlined above. In contrast to prior Examples 3A-C, a different substrate was used in Examples 4A-D. In Examples 4A-D, the substrate used was a dental implant offered by Applicant under the name T3®, but the implant was covered with a carbon nanotube surface. The nanotubes are visible in FIGS. 5A-C. An example of a nanotube structure on a dental implant, created by the Applicant, is disclosed in U.S. Patent Pub. No. 2017/0042682, which is incorporated by reference herein in its entirety. It is understood that the substrate utilized in Examples 4A-D, or in any other example or deposition method disclosed herein, can be any of the implants disclosed in the '682 Publication. The present Examples 4A-D describe the effect of varying deposition time during the deposition process outlined above, using a dental implant with a nanotube structure, similar to as in the '682 Publication.

It was observed that a higher amount of silver nanoparticles was deposited on the substrate (e.g., dental implant with nanotubes) with increased deposition time. In other words, higher coverage of the nanotubes' surfaces by silver particles was observed with the increase of deposition time. The deposition time for each figure is listed above the figure. It was also observed that, when the deposition time was increased to 30 or 45 minutes (FIGS. 5C-D), the silver nanoparticles formed clusters and covered the underlying nanotube surfaces. As such, it is contemplated herein that deposition time can be varied using a substrate with a nanotube structure (e.g., dental implant with nanotubes) to alter the amount of silver nanoparticles deposited on the substrate.

Figure 6:
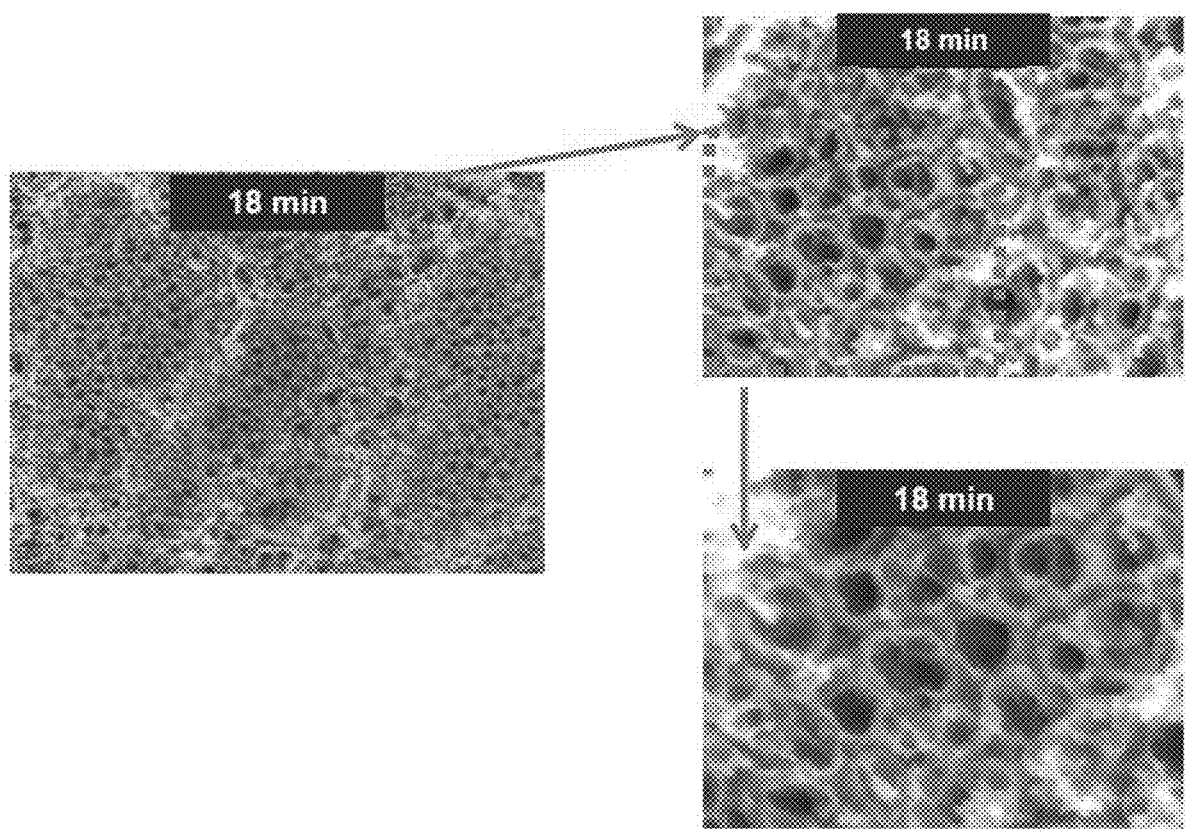
FIG. 6 are several close-up views of FIG. 5B.

FIG. 6 illustrates several relatively closer-up views of the nanotube surface of FIG. 5B, where the deposition time was about 18 minutes. The close-up views provide illustration as to areas in which silver nanoparticles were deposited on the nanotube substrate, with arrows pointing to areas of deposited silver nanoparticles, in certain instances.

EDS results demonstrated that the amount by weight percent of silver deposited on the nanotube substrate is as shown in the below Table 4.2. It is worthwhile to note that the lower standard deviations below indicate the silver particles were evenly distributed over the surface of the nanotubes.

TABLE 4.2

| Deposition Amount | 9 Minute Deposition | 18 Minute Deposition | 30 Minute Deposition | 45 Minute Deposition |
|---|---|---|---|---|
| Weight Percentage of Silver | 6.21 +/− 0.90% | 8.29 +/− 1.46% | 10.92 +/− 1.27% | 19.01 +/− 2.81% |

EXAMPLES 5A-B

Figure 7A:
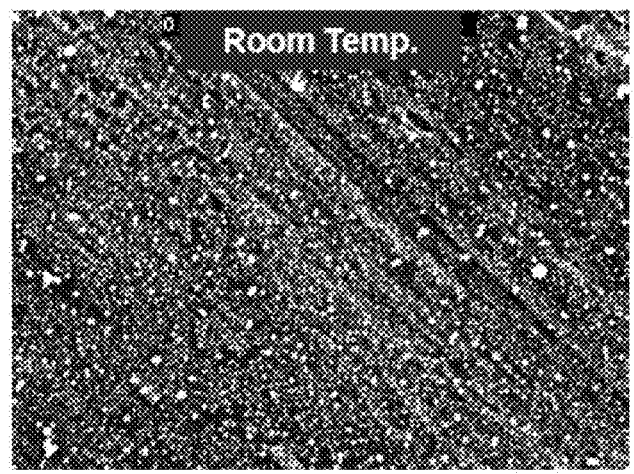
FIGS. 7A-B illustrate a substrate processed according to a fifth example of the deposition method of FIG. 1, where the deposition temperature was varied.
Figure 7B:
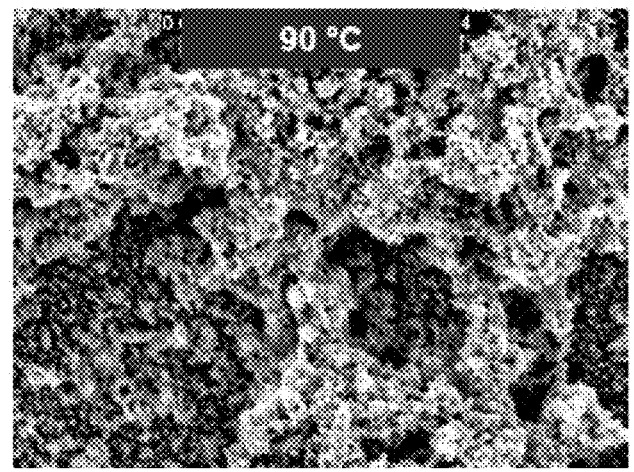

FIGS. 7A-B illustrate Examples 5A-B of the present disclosure, respectively. The deposition parameters for Examples 5A-B are shown in Table 5.1 below.

TABLE 5.1

| Deposition Time | $AgNO_3$ Concentration | $NaNO_3$ Concentration | Voltage | Variable |
|---|---|---|---|---|
| 90 seconds | 0.9 mM | 1.25 mM | 5 V | deposition temp |

As shown above, Examples 5A-B, illustrated in FIGS. 7A-B, respectively, demonstrate the effect of varying the deposition temperature of the electrolyte solution during the deposition process outlined above. The different deposition temperatures are shown above the respective figures. It was observed that, with an increase in deposition temperature, the amount and/or size of silver nanoparticles deposited on the substrate (e.g., dental implant) was increased. Thus, it is possible to vary the temperature of the electrolyte solution during deposition to vary the amount and/or size of silver nanoparticles deposited. The substrate used in Examples 5A-B was a machined Ti disk surface.

The above examples illustrate that various deposition parameters can be altered to alter the deposition of silver nanoparticles on a substrate, as detailed herein. It is to be appreciated that, while not disclosed above, any of these parameters can be used in combination with any other deposition parameter to alter the deposition of silver nanoparticles on a substrate.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A method of depositing nanoparticles on a dental implant comprising:
   preparing an electrolyte solution comprising an aqueous solution having silver nitrate ($AgNO_3$) and sodium nitrate ($NaNO_3$), wherein the aqueous solution has a concentration of between about 0.01 mM to about 50 mM, inclusive, $AgNO_3$, and wherein the aqueous solution has a concentration of between about 138 mM to about 1000 mM, inclusive, $NaNO_3$;
   positioning the dental implant within the electrolyte solution;
   applying an electric current to the electrolyte solution for a duration of time, thereby causing deposition of silver nanoparticles on a surface of the dental implant, the silver nanoparticles providing antimicrobial properties to the dental implant;
   rinsing the dental implant with deposited silver nanoparticles; and
   drying the dental implant with deposited silver nanoparticles in an oven between about 95° C. to about 105° C., inclusive for a period of time between about 20 minutes to about 40 minutes, inclusive.

2. The method of claim 1, further comprising controlling one or more of: deposition time, electrolyte solution temperature, an amount of electric current applied to the electrolyte solution, $AgNO_3$ concentration, and $NaNO_3$ concentration to control a size, quantity, and/or deposition location of silver nanoparticles on the surface of the dental implant.

3. The method of claim 1, further comprising maintaining a temperature of the electrolyte solution at anywhere between about 18-30° C. during the deposition of silver nanoparticles.

4. The method of claim 1, further comprising stirring the aqueous solution at a rate of anywhere between about 100-1000 RPM prior to the deposition of silver nanoparticles.

5. The method of claim 1, wherein the silver nanoparticles have broad spectrum antimicrobial properties against Gram-negative and Gram-positive bacteria, and a low microorganism resistance probability.

6. The method of claim 1, wherein a majority of the dental implant is coated with the silver nanoparticles.

7. The method of claim 1, wherein an amount by weight percentage of the silver nanoparticles on the surface of the dental implant is between 0.1 wt % and 25.0 wt %, inclusive.

8. The method of claim 1, wherein the silver nanoparticles are deposed on substantially all of the surface of the dental implant.

9. The method of claim 1, wherein the silver nanoparticles are substantially evenly distributed on the surface of the dental implant and with a substantial absence of silver nanoparticles having a size in at least one dimension over a predetermined size threshold.

10. The method of claim 9, wherein the predetermined size threshold is selected from between 0.1 nm and 50 nanometers in at least one dimension.

11. The method of claim 9, wherein the predetermined size threshold is selected from between 0.1 nm and 100 nanometers in at least one dimension.

12. The method of claim 9, wherein the predetermined size threshold is selected from between 50 nm and 100 nanometers in at least one dimension.

13. The method of claim 9, wherein the predetermined size threshold is selected from between 50 nm and 500 nanometers in at least one dimension.

14. The method of claim 9, wherein the predetermined size threshold is selected from between 100 nm and 500 nanometers in at least one dimension.

15. The method of claim 9, further comprising placing the dental implant through an ultrasonication process to remove silver nanoparticles having a size in at least one dimension over a predetermined size threshold.

16. A method of depositing nanoparticles on a dental implant comprising:
   preparing an electrolyte solution comprising an aqueous solution having silver nitrate ($AgNO_3$) and sodium nitrate ($NaNO_3$) wherein the aqueous solution has a concentration of between about 0.01 mM to about 50 mM, inclusive, $AgNO_3$, and, wherein the aqueous solution has a concentration of between about 138 mM to about 1000 mM, inclusive, $NaNO_3$;
   positioning the dental implant within the electrolyte solution; and
   applying an electric current to the electrolyte solution for a duration of time, thereby causing deposition of silver nanoparticles on an external surface of the dental implant, wherein the silver nanoparticles are substantially evenly distributed on the external surface of the dental implant and with a substantial absence of silver nanoparticles having a size in at least one dimension over a predetermined size threshold.

17. A method of depositing nanoparticles on a dental implant comprising:
   preparing an electrolyte solution comprising an aqueous solution having silver nitrate ($AgNO_3$) and sodium nitrate ($NaNO_3$) wherein the aqueous solution has a concentration of between about 0.01 mM to about 50 mM, inclusive, $AgNO_3$, and, wherein the aqueous solution has a concentration of between about 138 mM to about 1000 mM, inclusive, $NaNO_3$;
   positioning the dental implant within the electrolyte solution; and
   applying an electric current to the electrolyte solution for a duration of time, thereby causing deposition of silver nanoparticles on a surface of the dental implant; and
   controlling one or more of: deposition time, electrolyte solution temperature, an amount of electric current applied to the electrolyte solution, $AgNO_3$ concentration, and $NaNO_3$ concentration to control a size, quantity, and/or deposition location of silver nanoparticles on the surface of the dental implant.

* * * * *